United States Patent
Yokoi et al.

(10) Patent No.: US 10,124,092 B2
(45) Date of Patent: Nov. 13, 2018

(54) AIR LEAK DETECTION DEVICE AND ELECTRICALLY POWERED SUCTION EQUIPMENT PROVIDED THEREWITH

(71) Applicant: SENKO MEDICAL INSTRUMENT Mfg. Co., Ltd., Tokyo (JP)

(72) Inventors: Hiroshi Yokoi, Tokyo (JP); Norihisa Ichikawa, Tokyo (JP); Souichi Katsuta, Tokyo (JP); Masahiro Kihara, Tokyo (JP)

(73) Assignee: SENKO MEDICAL INSTRUMENT MFG. CO., LTD., Tokyo (JP)

(*) Notice: Subject to any disclaimer, the term of this patent is extended or adjusted under 35 U.S.C. 154(b) by 556 days.

(21) Appl. No.: 14/760,932

(22) PCT Filed: Jan. 17, 2014

(86) PCT No.: PCT/JP2014/050842
§ 371 (c)(1),
(2) Date: Jul. 14, 2015

(87) PCT Pub. No.: WO2014/112598
PCT Pub. Date: Jul. 24, 2014

(65) Prior Publication Data
US 2015/0343120 A1    Dec. 3, 2015

(30) Foreign Application Priority Data

Jan. 18, 2013  (JP) ................................. 2013-007155

(51) Int. Cl.
*A61M 1/00*    (2006.01)

(52) U.S. Cl.
CPC ........ *A61M 1/0013* (2013.01); *A61M 1/0025* (2014.02); *A61M 1/0031* (2013.01);
(Continued)

(58) Field of Classification Search
CPC combination set(s) only.
See application file for complete search history.

(56) References Cited

U.S. PATENT DOCUMENTS 4,617,020 A    10/1986  Kurtz
4,654,029 A *  3/1987   D'Antonio .......... A61M 1/0031
                                                   600/584

(Continued)

FOREIGN PATENT DOCUMENTS

JP    61-98263 A    5/1986
JP    02-8742 B     2/1990
(Continued)

OTHER PUBLICATIONS

Partial Supplementary European Search Report dated Nov. 7, 2016 for the corresponding European Patent Application No. 14740129.3.
(Continued)

*Primary Examiner* — Tatyana Zalukaeva
*Assistant Examiner* — Guy K Townsend
(74) *Attorney, Agent, or Firm* — Leason Ellis LLP

(57) ABSTRACT

An air leak detection device is applied to a thoracic cavity drainage system which, by using negative pressure generated by a vacuum source, aspirates gas in the thoracic cavity of a patient via a water seal chamber in which liquid is received. The pressure between the vacuum source and the water seal chamber is measured by a pressure sensor, and the occurrence of air bubbles created in the water seal chamber is detected on the basis of fluctuations of this pressure.

5 Claims, 3 Drawing Sheets

(52) U.S. Cl.
CPC . *A61M 2205/15* (2013.01); *A61M 2205/3331* (2013.01); *A61M 2205/3334* (2013.01); *A61M 2210/101* (2013.01)

(56) References Cited

U.S. PATENT DOCUMENTS

| | | | |
|---|---|---|---|
| 4,685,908 A | 8/1987 | Kurtz | |
| 5,562,608 A * | 10/1996 | Sekins | A61M 16/0486 604/20 |
| 5,989,234 A * | 11/1999 | Valerio | A61M 1/0013 604/319 |
| 6,544,192 B2 * | 4/2003 | Starr | A61B 5/087 600/532 |
| 7,207,946 B2 * | 4/2007 | Sirokman | A61M 1/0013 600/529 |
| 7,887,585 B2 * | 2/2011 | Gonzalez | A61B 17/12022 623/9 |
| 9,622,752 B2 * | 4/2017 | Gonzalez | A61B 17/12022 |
| 2003/0212337 A1 | 11/2003 | Sirokman | |
| 2011/0201956 A1 * | 8/2011 | Alferness | A61B 1/267 600/532 |
| 2013/0110057 A1 * | 5/2013 | Croteau | A61M 1/0031 604/318 |
| 2015/0343120 A1 * | 12/2015 | Yokoi | A61M 1/0013 604/318 |
| 2017/0224901 A1 * | 8/2017 | Niimi | A61M 1/3666 |
| 2017/0232182 A1 * | 8/2017 | Niimi | A61M 1/3666 604/66 |

FOREIGN PATENT DOCUMENTS

| | | |
|---|---|---|
| JP | 2000-060963 A | 2/2000 |
| WO | WO-2011/118888 A | 9/2011 |

OTHER PUBLICATIONS

International Search Report dated Apr. 8, 2014 for the corresponding PCT Application No. PCT/JP2014/050842.

* cited by examiner

AIR LEAK DETECTION DEVICE AND ELECTRICALLY POWERED SUCTION EQUIPMENT PROVIDED THEREWITH

CROSS-REFERENCE TO RELATED PATENT APPLICATIONS

This application is a U.S. National Phase Application under 35 U.S.C. § 371 of International Patent Application No. PCT/JP2014/050842, filed Jan. 17, 2014, and claims the benefit of Japanese Patent Application No. 2013-007155, filed Jan. 18, 2013, all of which are incorporated by reference in their entirety herein. The International Application was published in Japanese on Jul. 24, 2014 as International Publication No. WO/2014/112598 under PCT Article 21 (2).

FIELD OF THE INVENTION

The present invention relates to an air leak detection device that is capable of detecting air leak in which air is leaking into the thoracic cavity of a patient, and to an electrically powered suction equipment that is provided with such a device.

BACKGROUND OF THE INVENTION

After thorax surgery or during pneumothorax treatment, air leaks into a thoracic cavity of a patient. Such leaking of air into the thoracic cavity of the patient is generally termed air leak. In order to discharge to the exterior of the patient's body air that has leaked into his thoracic cavity or bodily fluid such as blood or the like that has accumulated in his thoracic cavity, procedures are performed to connect a thoracic cavity drain bag to a drain tube that is indwelt in the thoracic cavity of the patient after thoracic surgery or during pneumothorax treatment, and also to connect an suction equipment to this thoracic cavity drain bag so as to suck air that has leaked into the thoracic cavity and/or bodily fluid such as blood or the like that has accumulated in the thoracic cavity.

A drain chamber that traps liquid such as bodily fluid or the like that has been sucked from the thoracic cavity and a water seal chamber that contains a liquid such as water and thereby prevents reverse flow of external air toward the thoracic cavity are formed in the thoracic cavity drain bag. Air consequent upon air leak that has been sucked from the thoracic cavity passes through the liquid in the water seal chamber and is led to the exterior. When air passes through the liquid in the water seal chamber, air bubbles are generated. Accordingly, by a health care attendant observing air bubbles that are generated in the water seal chamber, it is possible to check upon the frequency and the state of occurrence of air leak and thus to ascertain the state of recovery of the patient, and thereby it is possible to decide about the timing for changing the drainage of the thoracic cavity from suction to simple gravity drainage, and the timing for removal of the drain tube. However it is difficult to observe the generation of air bubbles over time, since the frequency of generation of air bubbles in the water seal chamber decreases along with the progression of healing of the air leak.

Thus, as a detection device that detects air bubbles in the water seal chamber, a detection device has been proposed (refer to Patent Document #1) that detects air bubbles in the water seal chamber with an optical sensor, instead of by employing visual inspection. Moreover, a device is per se known (refer to Patent Document #2) that calculates the total amount of sucked air and liquid from the operational state of the vacuum pump, and that calculates the amount of sucked air by subtracting the amount of liquid accumulated in the drain chamber of the thoracic cavity drain device from this total sucked amount. Apart from the above, Patent Document #3 may be considered as being a document having some relevance to the present invention.

CITATION LIST

Patent Literature

Patent Document #1: JP1986-98263A.
Patent Document #2: JP2000-60963A.
Patent Document #3: PCT Publication 2011/118888.

Since the device of Patent Document #1 is a system that employs an optical sensor, accordingly there are the problems that, not only is it comparatively high in price, but also its detection of air bubbles experiences influence from the surrounding environment, such as the brightness of the illumination around the device and so on. Moreover, with Patent Document #2, there is the problem that a device for measuring the amount of liquid accumulated in the drain chamber is required in order for the device of the citation to calculate the air amount.

Accordingly, the object of the present invention is to provide an air leak detection device that is capable of detecting leakage of air into the body of a patient without any requirement for observation of the air bubbles in the water seal chamber, and to provide an electrically powered suction equipment that includes such an air leak detection device.

SUMMARY OF THE INVENTION

Solution to Problem

A first air leak detection device according to the present invention is applied to a thoracic cavity drain system which, by utilizing negative pressure generated by a vacuum source, sucks gas within a thoracic cavity of a patient via a water seal chamber in which liquid is received, and is provided between the vacuum source and the water seal chamber, and comprises: a pressure measurement device configured to measure a pressure between the vacuum source and the water seal chamber; and an air bubble detection device configured to detect occurrence of air bubbles created in the water seal chamber based on pressure fluctuations measured by the pressure measurement device.

When, along with leakage of air, air bubbles are generated in the water seal chamber, pressure fluctuations occur between the water seal chamber and the vacuum source. Since, according to this air leak detection device, the pressure between the water seal chamber and the vacuum source is measured, and the generation of air bubbles is detected on the basis of fluctuations of this pressure, accordingly it is possible to detect leakage of air into the thorax of the patient without observation of the air bubbles in the water seal chamber.

As one aspect of this air leak detection device according to the first aspect of the present invention, there may be further included: a storage device configured to store a detection result of occurrence of air bubbles by the air bubble detection device, and a magnitude of the pressure fluctuations when occurrence of air bubbles is detected; and an output control device configured to output to a predetermined output device a correlation between the detection result and the magnitude of the pressure fluctuations stored by the storage device. According to this aspect, a correlation is established between the occurrence of air bubbles and the magnitude of the pressure fluctuations, and this correlation is outputted to the output device. Due to this, by not only evaluating the frequency of occurrence of air leak, but also by quantitatively evaluating the magnitude of the associated pressure fluctuations, it is possible to determine the type of air leak, for example to distinguish between air leak that occurs during sneezing or coughing and air leak that occurs during normal respiration or conversation.

And an electrically powered suction equipment according to the present invention is connected to a thoracic cavity drain bag to which is provided a water seal chamber in which liquid is received, and sucks gas within a thoracic cavity of a patient via the water seal chamber of the thoracic cavity drain bag, and includes: a an electrically operated vacuum pump configured to generate negative pressure; a pressure measurement device configured to measure the pressure between the water seal chamber and the electrically operated vacuum pump; a pump control device configured to control the electrically operated vacuum pump based on a pressure measured by the pressure measurement device; and an air bubble detection device configured to detect occurrence of air bubbles generated in the water seal chamber based on pressure fluctuations measured by the pressure measurement device.

Since, according to this electrically powered suction equipment, the pressure between the water seal chamber and the electrically operated vacuum pump is measured, and the generation of air bubbles is detected on the basis of these pressure fluctuations, accordingly it is possible to detect leakage of air into the thorax of the patient without observation of the air bubbles in the water seal chamber. Moreover, since it is possible to detect the generation of air bubbles by employing the pressure measurement device that is also used for controlling the electrically operated pump, accordingly there is the advantageous aspect that it becomes unnecessary to employ any dedicated pressure measurement device for detecting the generation of air bubbles.

A second air leak detection device according to the present invention is applied to a thoracic cavity drain system which, by utilizing negative pressure generated by a vacuum source, sucks gas within a thoracic cavity of a patient via a water seal chamber in which liquid is received, and is provided between the vacuum source and the water seal chamber, and comprises: a flow rate measurement device configured to measure the flow rate from the water seal chamber toward the vacuum source; and an air bubble detection device configured to detect occurrence of air bubbles created in the water seal chamber based on flow rate fluctuations measured by the flow rate measurement device.

When, along with leakage of air, air bubbles are generated in the water seal chamber, flow rate fluctuations occur between the water seal chamber and the vacuum source. Since, according to this air leak detection device, the flow rate from the water seal chamber toward the vacuum source is measured, and the generation of air bubbles is detected on the basis of fluctuations of this flow rate, accordingly it is possible to detect leakage of air into the thorax of the patient without observation of the air bubbles in the water seal chamber.

As one aspect of this air leak detection device according to the second aspect of the present invention, there may be further included: a storage device configured to store a detection result of occurrence of air bubbles by the air bubble detection device, and a magnitude of the flow rate fluctuations when occurrence of air bubbles is detected; and an output control device configured to output to a predetermined output device a correlation between the detection result and the magnitude of the flow rate fluctuations stored by the storage device. According to this aspect, a correlation is established between the generation of air bubbles and the magnitude of the flow rate fluctuations, and this correlation is outputted to the output device. Due to this, by not only evaluating the frequency of occurrence of air leak, but also by quantitatively evaluating the magnitude of the flow rate fluctuations, it is possible to determine the type of air leak, for example to distinguish between air leak that occurs during sneezing or coughing and air leak that occurs during normal respiration or conversation.

DETAILED DESCRIPTION OF THE INVENTION

Embodiment #1

Figure 1:
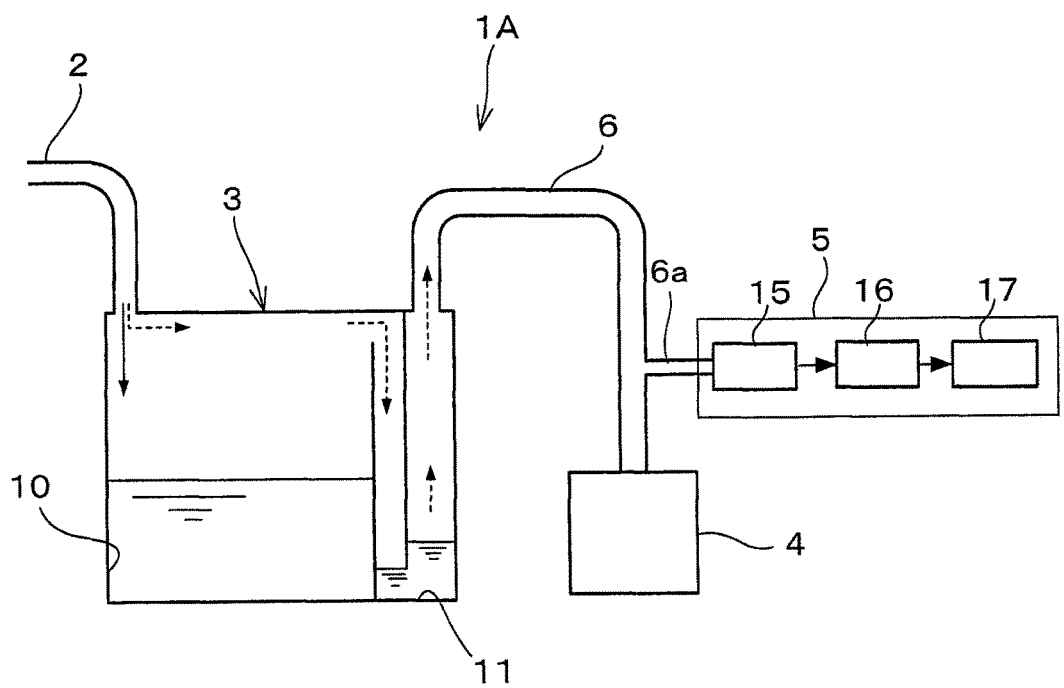
FIG. 1 is a figure schematically showing the overall structure of a thoracic cavity drain system to which an air leak detection device according to a first embodiment of the present invention is applied.

As shown in FIG. 1, a thoracic cavity drain system 1A is employed for discharging air that has leaked into the thoracic cavity of a patient, or liquid such as blood or the like that has accumulated within the thoracic cavity, to the exterior of the body of the patient. This thoracic cavity drain system 1A comprises a drain tube 2 that is indwelt in the thoracic cavity of a patient who has experienced thoracic surgery or of a patient under pneumothorax treatment, a thoracic cavity drain bag 3 connected to this drain tube 2, a vacuum source 4 connected to the thoracic cavity drain bag 3 via an suction circuit 6, and an air leak detection device 5 connected to the suction circuit 6 and provided between the thoracic cavity drain bag 3 and the vacuum source 4. It should be understood that, in order to prevent aspiration at excessive negative pressure in the suction circuit 6, a pressure regulation chamber that is communicated to the atmosphere and that is filled with liquid is also connected in the system, but this feature is not shown in the drawing.

One end of the drain tube 2 is inserted into the thoracic cavity of the patient, while its other end is connected to the thoracic cavity drain bag 3. The thoracic cavity drain bag 3 has the same structure as a commercially available one of the single use type. A drain chamber 10 that traps liquid such as bodily fluids and the like sucked from the thoracic cavity and a water seal chamber 11 that contains a liquid such as water or the like and prevents reverse flow of external air into the thoracic cavity are formed in the thoracic cavity drain bag 3. Due to the negative pressure generated by the vacuum source 4, liquid within the thoracic cavity of the patient is trapped in the drain chamber as shown by the solid line arrow sign, and moreover gas that has leaked into the thoracic cavity of the patient is conducted to the suction circuit 6 via the water seal chamber 11 as shown by the broken line arrow signs. Accordingly, if an air leak has occurred within the thoracic cavity of the patient, air bubbles are generated in the water seal chamber 11, since this air passes through the water seal chamber 11.

Figure 2:
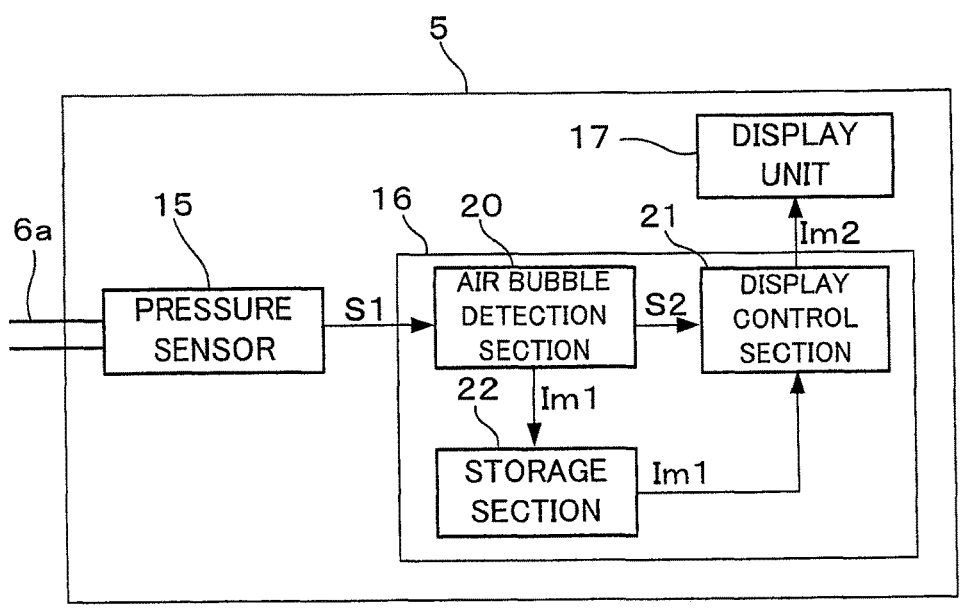
FIG. 2 is a block diagram showing the details of the air leak detection device of FIG. 1.

As also shown in FIG. 2, the air leak detection device 5 comprises: a pressure sensor 15 that serves as a pressure measurement device and is connected to a branch conduit 6a that branches off from the suction circuit 6; a calculation processing unit 16 that is electrically connected to the pressure sensor 15; and a display device 17 that serves as an output device that displays information outputted from the calculation processing unit 16. The pressure sensor 15 measures the pressure between the water seal chamber 11 and the vacuum source 4, and outputs a signal S1 corresponding to this pressure. This signal S1 outputted from the pressure sensor 15 is inputted to the calculation processing unit 16.

The calculation processing unit 16 comprises a computer, and provides logical sections as shown in the figure by executing a predetermined program. An air bubble detection section 20 constituted by the calculation processing unit is also described as the "air bubble detection device"; a display control section 21 is also described as the "output control device"; and a storage section 22 is also described as the "storage device".

The air bubble detection section 20 monitors the output signal Si of the pressure sensor 15, and detects occurrence of air bubbles within the water seal chamber 11 on the basis of pressure fluctuations measured by the pressure sensor 15, in other words detects air leak. As the method for this detection, it is determined that air bubbles are being generated if, in a predetermined measurement time interval (for example 10 msec), a reduction of negative pressure greater than or equal to some fixed value (for example greater than or equal to 0.5 hPa) takes place. Reduction of the negative pressure is defined as a change of pressure in the direction towards atmospheric pressure, while increase of the negative pressure is defined as a change of pressure in the direction away from atmospheric pressure. In this case, irrespective of the actual number of air bubbles, the pressure fluctuation during the measurement time interval counts as one episode of air bubble occurrence. The pressure fluctuation may be calculated immediately from one moment to the next on the basis of measurements by the pressure sensor, or may be calculated on the basis of the average of some number of measured values.

Since there are many cases in which a number of air bubbles are generated together, in order to distinguish between one episode of generation of air bubbles and the next, this is done by counting the fluctuations within a fixed time interval (for example, one second) from the start of pressure fluctuation together as being one episode, and by counting the subsequent pressure fluctuations as being the next episode of generation of air bubbles. As a matter of course, instead of this condition or in combination therewith, it would also be possible to distinguish between one episode of generation of air bubbles and the next episode of generation of air bubbles by counting pressure fluctuations that are generated after a fixed time period (for example two seconds) or greater has elapsed from when it has stopped being decided that the pressure fluctuations constitute generation of air bubbles, as being the next episode of generation of air bubbles.

When the air bubble detection section 20 detects the generation of air bubbles, the air bubble detection section sends an air bubble detection signal S2 to the display control section 21, and also sends to the storage section 22 information Im1 including this result of detection of the generation of air bubbles and the magnitude of the pressure fluctuations when this detection was made. The storage section 22 stores this information Im1 and time information in mutual correlation. And, upon receipt of the air bubble detection signal S2, the display control section 21 reads out the information Im1 stored in the storage section 22, creates image information Im2 specifying display details to be displayed corresponding to this information Im1, in other words specifying display details in which the correlation between the results of detection of generation of air bubbles and the magnitude of the pressure fluctuations detected at this time is shown, and sends this image information Im2 to the display device 17. And, due to the display control section 21 sending this image information Im2 to the display device 17, an image that corresponds to the image information Im2 is outputted upon the display device 17. For example, an image in graphic format in which the correlation between the generation of air bubbles and the magnitude of the pressure fluctuations is shown visually may be outputted upon the display device 17.

It is possible for the display control section 21 to receive actuation by the operator, and, on the basis of this actuation, information Im1 stored in the storage section 22 in correlation with time information may be read out as desired and displayed upon the display device 17. Due to this, even without observing the details displayed upon the display device 17 in real time, it is still possible to analyze and evaluate the frequency of generation of air bubbles and the magnitude of the pressure fluctuations when they were detected, later on after the event.

According to this air leak detection device 5, since the pressure between the water seal chamber 11 and the vacuum source 4 is measured, and the generation of air bubbles is detected on the basis of fluctuations of this pressure, accordingly it is possible to detect air leak of the patient without observation of the air bubbles in the water seal chamber 11. Moreover, since a correlation between the generation of air bubbles and the magnitude of the pressure fluctuations is made, and this correlation is outputted upon the display device 17, accordingly, by not only evaluating the frequency of occurrence of air leak but also quantitatively evaluating the magnitude of the pressure fluctuations, it is possible to determine the type of air leak; for example, it is possible to distinguish between air leak that occurs during coughing and sneezing, and air leak that occurs during normal respiration or conversation.

Embodiment #2

Next, a second embodiment of the present invention will be explained with reference to FIG. 3. This second embodiment is one in which the present invention is implemented as an electrically powered suction equipment that is equipped with an air leak detection device 5 according to the first embodiment. In the following, the same reference symbols will be appended to structures that are the same as in the first embodiment, and explanation thereof will be omitted.

Figure 3:
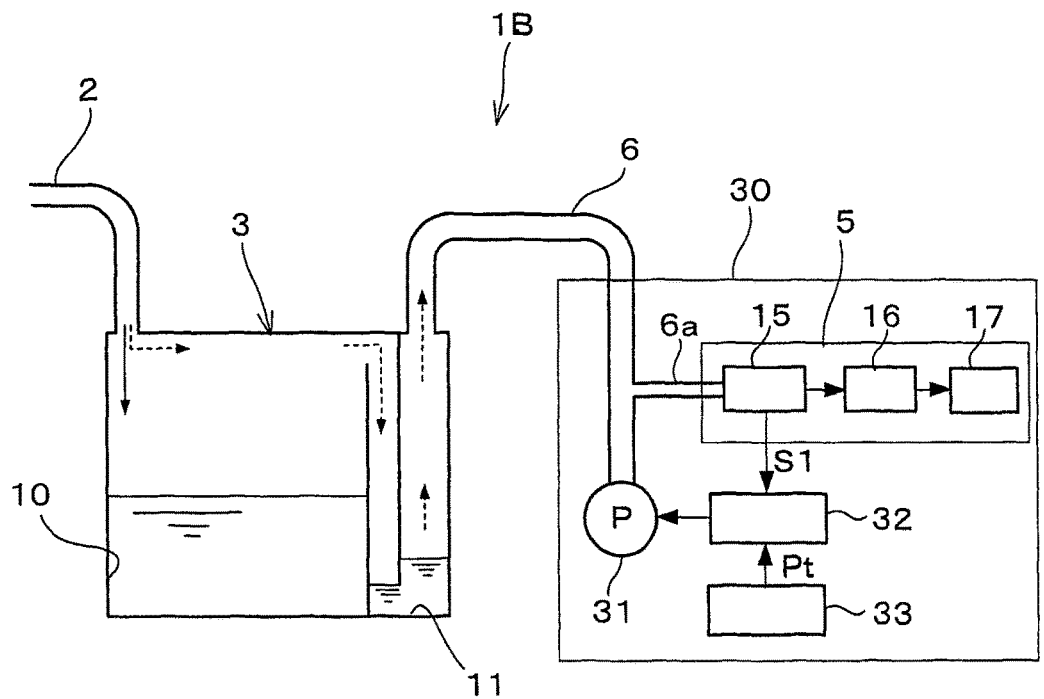
FIG. 3 is a figure schematically showing the overall structure of a thoracic cavity drain system to which an electrically powered suction equipment according to a second embodiment of the present invention is applied.

As shown in FIG. 3, a thoracic cavity drain system 1B comprises a thoracic cavity drain bag 3 that is connected to a drain tube 2, and an electrically powered suction equipment 30 that is connected to the thoracic cavity drain bag 3 via an suction circuit 6. The electrically powered suction equipment 30 comprises an electrically powered vacuum pump 31 that is connected to the suction circuit 6, a pump control section 32 that controls the electrically operated vacuum pump 31, and an aspiration condition setting unit 33 that sets conditions for suction. It is possible for the suction condition setting unit 33 to receive actuation by the operator for setting a set pressure during suction, and, upon receipt of such actuation by the unit 33, the unit 33 sends the set pressure Pt to the pump control section 32. And an air leak detection device 5 as described above is provided between the water seal chamber 11 and the electrically operated vacuum pump 31. The output signal of the pressure sensor 15 included in the air leak detection device 5 is sent to the pump control section 32. The pump control section 32 acquires the pressure between the water seal chamber 11 and the electrically operated vacuum pump 31 on the basis of the output signal S1 of the pressure sensor 15, calculates the deviation between this pressure and the set pressure Pt set by the suction condition setting unit 33, and controls the electrically operated vacuum pump 31 so as to reduce this deviation. The pump control section 32 is also described as the "pump control device".

The details of the processing performed by the leak detection device 5 are the same as in the first embodiment. Accordingly, this electrically powered suction equipment 30 provides similar beneficial effects to those of the first embodiment. In other words, since the electrically powered suction equipment 30 measures the pressure between the water seal chamber 11 and the electrically operated vacuum pump 31 and the generation of air bubbles is detected on the basis of fluctuation of this pressure, accordingly it is possible to detect the occurrence of air leak into the patient without observation of the air bubbles in the water seal chamber 11. Moreover, since a correlation between the generation of air bubbles and the magnitude of the pressure fluctuations is outputted upon the display device 17, accordingly, not only is it possible to determine the frequency of occurrence of air leak, but also, by quantitatively evaluating the magnitude of the pressure fluctuations, it is possible to determine the type of air leak; for example, it is possible to distinguish between air leak that occurs during coughing and sneezing, and air leak that occurs during normal respiration or conversation. In particular there is the advantageous aspect that, with this electrically powered suction equipment 30, it becomes unnecessary to provide any dedicated pressure measurement device for detecting the generation of air bubbles, since it is possible to detect the generation of air bubbles by utilizing the pressure sensor 15 that is also employed for control of the electrically operated vacuum pump 31.

Embodiment #3

Figure 4:
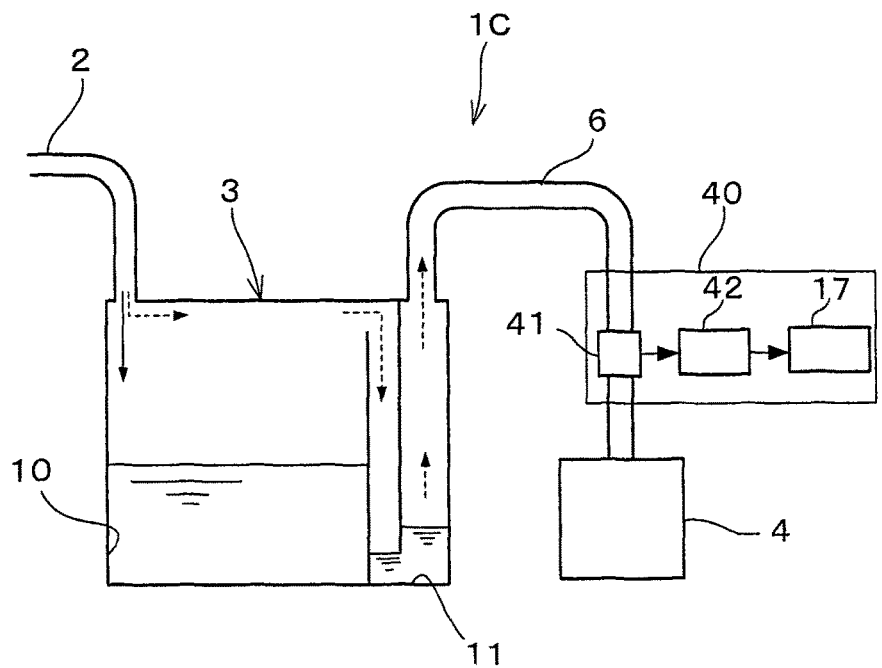
FIG. 4 is a figure schematically showing the overall structure of a thoracic cavity drain system to which an air leak detection device according to a third embodiment of the present invention is applied.
Figure 5:
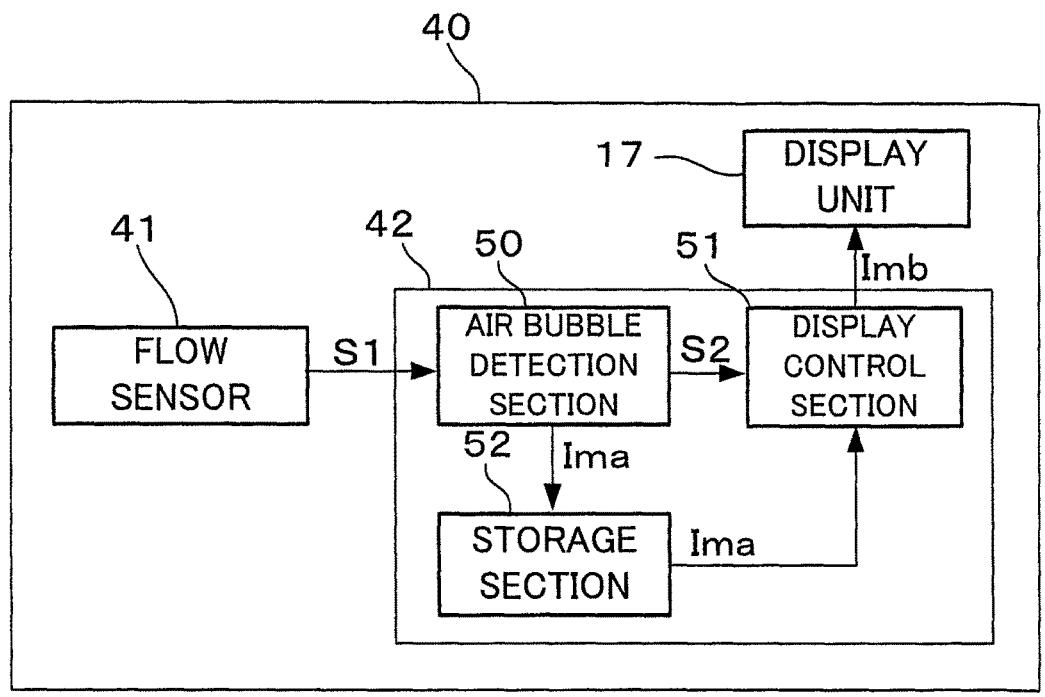
FIG. 5 is a block diagram showing the details of the air leak detection device of FIG. 4.

Next, a third embodiment of the present invention will be explained with reference to FIGS. 4 and 5. This third embodiment is characterized in that the flow rate from the water seal chamber toward the vacuum source is measured, and the generation of air bubbles is detected on the basis of fluctuations of this flow rate. The thoracic cavity drain system 1C shown in FIG. 4 is the same as that of the first embodiment, except that an air leak detection device 40 is provided, instead of the air leak detection device 5 according to the first embodiment. In the following, the same reference symbols will be appended in FIG. 4 to structures that are the same as in the first or the second embodiment, and explanation thereof will be omitted.

The air leak detection device 40 is provided between the water seal chamber 11 and the vacuum source 4. And a flow rate sensor 41 is provided to the suction circuit 6, and serves as a flow rate measurement device that measures the flow rate from the water seal chamber 11 toward the vacuum source 4. As also shown in FIG. 5, the flow rate sensor 41 outputs a signal S1 corresponding to the flow rate, with this output signal S1 being inputted to a calculation processing unit 42 that is built around a computer. The generation of air bubbles is detected by the calculation processing unit 42, and the result of this detection is outputted to the display device 17. The details of the processing by the calculation processing unit 42 are the same as those explained in connection with the first embodiment, except that the generation of air bubbles is detected on the basis of fluctuations of the flow rate. In other words, as shown in FIG. 5, an air bubble detection section 50 that serves as an air bubble detection device, a display control section 51 that serves as an output control device, and a storage section 52 that serves as a storage device are constituted by a predetermined program being executed by the calculation processing unit 42.

The air bubble detection section 50 monitors the output signal S1 of the flow rate sensor 41, and detects the generation of air bubbles in the water seal chamber 11 on the basis of fluctuations of the flow rate measured by the flow rate sensor 41. As the method for performing this detection, it may be determined that air bubbles are being generated if the speed of the flow rate fluctuations is greater than or equal to a reference value. Or, as alternatives, it would also be possible to determine that air bubbles are occurring if any one of (1) the magnitude of the change of the flow rate, or (2) the magnitude of the change of the flow rate per unit time (i.e. the change speed), or (3) continuation of the flow for at least a fixed time interval, has become greater than or equal to a value which is set in advance, or on the basis of a condition which is a combination of the above conditions.

Distinguishing between one episode of air bubble generation and the next episode of air bubble generation is performed by counting the fluctuations within a fixed time period from the start of flow rate fluctuation greater than or equal to some fixed value as being one episode of air bubble generation, and by counting subsequent flow rate fluctuations as being the next episode of air bubble generation. As a matter of course, instead of this condition or in combination therewith, it would also be possible to distinguish between one episode of generation of air bubbles and the next episode of generation of air bubbles by counting pressure fluctuations that are generated after a predetermined time period has elapsed from when it has stopped being decided that the flow rate fluctuations constitute generation of air bubbles, as being the next episode of generation of air bubbles.

When the air bubble detection section 50 detects the generation of air bubbles, the air bubble detection section sends an air bubble detection signal S2 to the display control section 51, and also sends to the storage section 52 information Ima including this result of detection of generation of air bubbles and the magnitude of the flow rate fluctuations when this detection was made. The storage section 52 stores this information Ima and time information in mutual correlation. And, upon receipt of the air bubble detection signal S2, the display control section 51 reads out the information Ima stored in the storage section 52, creates image information Imb specifying display details to be displayed corresponding to this information Ima, in other words specifying display details in which the correlation between the results of detection of generation of air bubbles and the magnitude of the flow rate fluctuations detected at this time is shown, and sends this image information Imb to the display device 17. And, due to the display control section 51 sending this image information Imb to the display device 17, an image that corresponds to the image information Imb is outputted upon the display device 17. For example, an image in graphic format or the like in which the correlation between the generation of air bubbles and the magnitude of the flow rate fluctuations is shown visually may be outputted upon the display device 17.

It is possible for the display control section 51 to receive actuation by the operator, and, on the basis of this actuation, the information Ima stored in the storage section 52 in correlation with time information may be read out as desired and displayed upon the display device 17. Due to this, even without observing the details displayed upon the display device 17 in real time, it is still possible to analyze and evaluate the frequency of generation of air bubbles and the magnitude of the flow rate fluctuations when they were detected, later on after the event.

According to this air leak detection device 40, since the flow rate from the water seal chamber 11 toward the vacuum source 4 is measured, and the generation of air bubbles is detected on the basis of fluctuations of this flow rate, accordingly it is possible to detect leakage of air into the patient without observation of the air bubbles in the water seal chamber 11. Moreover, since a correlation between the generation of air bubbles and the magnitude of the flow rate fluctuations is made, and this correlation is outputted upon the display device 17, accordingly, by not only evaluating the frequency of occurrence of air leak but also quantitatively evaluating the magnitude of the flow rate fluctuations, it is possible to determine the type of air leak; for example, it is possible to distinguish between air leak that occurs during coughing and sneezing, and air leak that occurs during normal respiration or conversation.

The present invention is not to be considered as being limited to the embodiments described above; it can be implemented in various different forms, provided that the range of the gist of the present invention is adhered to. Moreover while, in the first or the second embodiment described above, the occurrence of air bubbles was determined upon when reduction of the negative pressure greater than a fixed value occurred for a predetermined fixed measurement time interval, it would be possible to change the standard and the method for determining upon the occurrence of air bubbles. For example, it would also be possible to determine upon the occurrence of air bubbles when any one of (1) the magnitude of the change of the pressure, or (2) the magnitude of the change of the pressure per unit time, or (3) the time that the decrease of the negative pressure has continued, has become greater than or equal to a value which is set in advance, or on the basis of a condition which is a combination of the above conditions. Moreover, it is possible to enhance the accuracy of determination of the occurrence of air bubbles for at least one of the conditions (1) through (3) by deciding that air bubbles are being generated according to either one of the two conditions (4) that pressure fluctuations of the negative pressure are generated both in the decrease direction and in the increase direction within a fixed time period, and (5) that the minimum value of the negative pressure when the pressure fluctuations are generated is smaller than some set pressure (i.e. is close to atmospheric pressure), or by combining those two conditions.

Any information may be displayed upon the display device 17, as desired. For example, it would also be possible to display the results of detecting the number of bubbles generated per unit time. In the first embodiment or the second embodiment, it would also be possible to count the number of air bubbles from the pressure fluctuations during one episode, and to calculate and output as the flow rate on the basis of the volume of one average air bubble which is set in advance. It would be acceptable to arrange to display the magnitude of the pressure fluctuations or of the flow rate fluctuations at the time point that the air bubbles are detected as an image or in character format; or it would also be acceptable to arrange to display the change chronologically. If the change is displayed chronologically in graphic format, then it would also be possible to provide this display upon the display device 17 with a time axis that is varied together with the frequency of detection of air bubbles, so that the higher the frequency of occurrence of air bubbles is, the shorter is the scale interval displayed along the time axis (for example, with full scale being one second), while the lower the frequency of occurrence of air bubbles is, the longer is the scale interval displayed along the time axis (for example, with full scale being one day). Moreover it would be possible, along with the time point of detection of air bubbles, also to display the magnitude of the pressure fluctuations or of the flow rate fluctuations. In this case, it would be possible for the user to apprehend the frequency and the level of generation of air bubbles intuitively and it would be useful to judge the level of recovery of the patient. Furthermore, it should be understood that the subject of output of the result of detection of air bubbles is not limited to being a display device. For example, it would also be possible to output audio information giving the correlation between the result of detection of air bubbles and the magnitude of the pressure fluctuations or of the flow rate fluctuations from an output device such as a speaker or the like.

The invention claimed is:

1. An air leak detection device for a thoracic cavity drain system comprising:
   a pressure measurement device configured to measure a pressure between a vacuum source and a water seal chamber, the vacuum source being configured to be connected to the air leak detection device; and
   an air bubble detection device configured to detect an occurrence of air bubbles created in the water seal chamber based on pressure fluctuations measured by the pressure measurement device, wherein
   the air bubble detection device is configured to determine that air bubbles have been created when a reduction of negative pressure within a predetermined period is greater than a fixed value, or when the negative pressure continues to decrease for a duration of time that is equal to or greater than a predetermined value,
   the vacuum source is configured to generate the negative pressure and suck gas within a thoracic cavity of a patient via the water seal chamber in which liquid is received, and
   the air leak detection device is configured to be provided between the vacuum source and the water seal chamber.

2. The air leak detection device according to claim 1, further comprising:
   a storage device configured to store a detection result of the occurrence of air bubbles by the air bubble detection device, a magnitude of the pressure fluctuations when occurrence of air bubbles is detected and time information in mutual correlation; and
   an output control device configured to output to a predetermined output device a correlation between the detection result and the magnitude of the pressure fluctuations stored by the storage device.

3. The air leak detection device according to claim 1, wherein
the vacuum source is an electrically powered suction equipment that is connected to a thoracic cavity drain bag to which is provided the water seal chamber the vacuum source further comprising:
an electrically operated vacuum pump configured to generate negative pressure; and
a pump control device configured to control the electrically operated vacuum pump based on a pressure measured by the pressure measurement device.

4. The air leak detection device according to claim 1, wherein
the air bubble detection device is configured to determine that air bubbles have been created when the pressure fluctuations of the negative pressure are generated both in a decreasing direction and in an increasing direction within a fixed time period, or when a minimum value of the negative pressure at a time the pressure fluctuations are generated is closer to atmospheric pressure than a set pressure.

5. The air leak detection device according to claim 4, wherein
the vacuum source is electrically powered suction equipment that is connected to a thoracic cavity drain bag to which is provided the water seal chamber, the vacuum source further comprising:
an electrically operated vacuum pump configured to generate negative pressure; and
a pump control device configured to control the electrically operated vacuum pump based on a pressure measured by the pressure measurement device.

\* \* \* \* \*